(12) United States Patent
Bar-Cohen et al.

(10) Patent No.: US 10,578,480 B2
(45) Date of Patent: Mar. 3, 2020

(54) MULTI-PROBE SYSTEM FOR MEASURING HEIGHT OF FLUID IN PIPES WITH STEADY-STATE AND TURBULENT FLOW CONDITIONS

(71) Applicant: CALIFORNIA INSTITUTE OF TECHNOLOGY, Pasadena, CA (US)

(72) Inventors: Yoseph Bar-Cohen, Pasadena, CA (US); Shyh-Shiuh Lih, Pasadena, CA (US); Hyeong Jae Lee, Pasadena, CA (US); Mircea Badescu, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 208 days.

(21) Appl. No.: 15/957,495

(22) Filed: Apr. 19, 2018

(65) Prior Publication Data

US 2018/0306633 A1    Oct. 25, 2018

Related U.S. Application Data

(60) Provisional application No. 62/489,910, filed on Apr. 25, 2017.

(51) Int. Cl.
*G01F 23/296* (2006.01)

(52) U.S. Cl.
CPC .... *G01F 23/2962* (2013.01); *G01N 2291/011* (2013.01); *G01N 2291/02425* (2013.01); *G01N 2291/02836* (2013.01); *G01N 2291/044* (2013.01); *G01N 2291/051* (2013.01); *G01N 2291/105* (2013.01); *G01N 2291/106* (2013.01)

(58) Field of Classification Search
CPC .............. G01F 23/296; G01F 23/2962; G01N 2291/02836
USPC ....................................................... 73/290 V
See application file for complete search history.

(56) References Cited

U.S. PATENT DOCUMENTS

| 5,670,710 A * | 9/1997 | Atkinson | G01F 23/2962 |
| | | | 73/290 V |
| 5,719,329 A * | 2/1998 | Jepson | G01F 1/24 |
| | | | 73/597 |
| 5,996,407 A * | 12/1999 | Hewitt | G01F 22/00 |
| | | | 73/290 V |

(Continued)

*Primary Examiner* — Nathaniel J Kolb
(74) *Attorney, Agent, or Firm* — Steinfl + Bruno LLP

(57) ABSTRACT

A multi-probe system for real-time measurement of a fluid level in a pipe with steady-state and turbulent flow conditions is presented. The multi-probe system includes a plurality of multiplexed transducers attached in a non-destructive fashion to walls of the pipe. Multiplexing of the transducers activate and deactivate the transducers in sequence to generate independent pairs of transmit and receive wave signals through the pipe. Each transmit and receive signal pair can be used to independently establish a time-of-flight from the transducer and back to the transducer as reflected by a surface of the fluid. The transducers can be arranged as longitudinal and/or circumferential arrays on the walls of the pipe. An algorithm that determines the time-of-flight eliminates received signals having an energy level lower than or equal to a predefined minimum energy level and eliminates any time-of-flight that is shorter than a minimum threshold time.

16 Claims, 11 Drawing Sheets

(56) References Cited

U.S. PATENT DOCUMENTS

| | | | |
|---|---|---|---|
| 6,212,943 B1 | 4/2001 | Maltby et al. | |
| 6,279,379 B1 | 8/2001 | Logue et al. | |
| 6,925,869 B2 * | 8/2005 | Senibi | G01F 23/2962 73/290 V |
| 6,925,870 B2 * | 8/2005 | Pappas | G01F 23/2962 73/290 V |
| 6,968,738 B2 * | 11/2005 | Atkinson | G01F 23/2962 73/290 V |
| 7,360,403 B2 | 4/2008 | Jones et al. | |
| 8,632,244 B2 | 1/2014 | Bar-Cohen et al. | |
| 9,404,891 B2 | 8/2016 | Lih et al. | |
| 9,586,234 B2 | 3/2017 | Bar-Cohen et al. | |
| 10,267,663 B2 * | 4/2019 | Skelding | G01F 15/02 |
| 2003/0061876 A1 * | 4/2003 | Atkinson | G01F 23/2962 73/290 V |
| 2004/0144170 A1 * | 7/2004 | Senibi | G01F 23/2962 73/290 V |
| 2005/0072226 A1 * | 4/2005 | Pappas | G01F 23/2962 73/290 V |
| 2008/0018199 A1 | 1/2008 | Trolier-McKinstry et al. | |
| 2014/0008304 A1 * | 1/2014 | Jansen | B01D 17/12 210/708 |
| 2016/0146653 A1 * | 5/2016 | Skelding | G01F 15/02 73/861.01 |

* cited by examiner

MULTI-PROBE SYSTEM FOR MEASURING HEIGHT OF FLUID IN PIPES WITH STEADY-STATE AND TURBULENT FLOW CONDITIONS

CROSS REFERENCE TO RELATED APPLICATIONS

The present application claims priority to and the benefit of co-pending U.S. provisional patent application Ser. No. 62/489,910 entitled "Multi-Probe System for Measuring Height of Water in Steam Pipes with Steady-State and Turbulent Flow Conditions", filed on Apr. 25, 2017, the disclosure of which is incorporated herein by reference in its entirety.

The present application is related to U.S. Pat. No. 8,632,244 B2 entitled "In-Service Monitoring of Steam Pipe Systems at High Temperatures" issued on Jan. 21, 2014, the disclosure of which is incorporated herein by reference in its entirety. The present application is also related to U.S. Pat. No. 9,404,891 B2 entitled "Apparatus for and Method of Monitoring Condensed Water in Steam Pipes at High Temperatures" issued on Aug. 2, 2016, the disclosure of which is incorporated herein by reference in its entirety. The present application is also related to U.S. Pat. No. 9,586,234 B2 entitled "High Temperature Ultrasonic Probe and Pulse-Echo Probe Mounting Fixture for Testing and Blind Alignment of Steam Pipes" issued on Mar. 7, 2017, the disclosure of which is incorporated herein by reference in its entirety.

STATEMENT OF GOVERNMENT GRANT

The invention described herein was made in the performance of work under a NASA contract NNN12AA01C, and is subject to the provisions of Public Law 96-517 (35 USC 202) in which the Contractor has elected to retain title.

TECHNICAL FIELD

The present disclosure relates to systems and methods for measuring fluid contents of piping systems in general, and particularly for measuring fluid contents under turbulent flow conditions.

BACKGROUND

Generally, steam pipes are used as part of a district heating system in many cities carrying steam from central power stations under the streets to heat, cool, or supply power to high rise buildings and businesses. Some businesses and facilities also use the delivered steam for cleaning and sterilization. In addition to providing space and water heating, the steam is used in numerous restaurants for food preparation, laundries and dry cleaners, as well as to power absorption chiller systems for air conditioning. One of the concerns to such a system is the excitation of water hammer that may lead to serious consequences including damaged vents, traps, regulators and piping. The water hammer is caused by accumulation of condensed water that is trapped in a portion of horizontal steam pipes. The velocity of the steam flowing over the condensed water causes ripples in the water creating buildup of turbulence resulting in the water formation of a solid mass or slug that fills the pipe. The slug of the condensed water can travel at the speed of the steam striking the first elbow that is encountered in its path. The force can be comparable to a hammer blow and can be sufficiently large to break the back surface of the elbow.

The above referenced U.S. Pat. Nos. 8,632,244 B2, 9,404,891 B2, and 9,586,234 B2, the disclosures of which are incorporated herein by reference in their entireties, describe systems and methods that can provide real-time monitoring of fluid level (e.g., height) in pipes that operate at high temperature and elevated pressure. Results of such monitoring can be provided to data handling systems for further action based on the results, and/or provided for display and monitoring purposes. According to such referenced patents, measurement of fluid height at a location inside the pipes is provided by a single piezoelectric transducer that launches an ultrasonic probe signal into the pipe, without mechanically penetrating the wall of the pipes. Reflected ultrasonic signals are captured by a transducer, which can be the same transducer that launched the probe signal. The reflected signals are subjected to data processing, which can include filtering, amplification, analog-to-digital conversion and autocorrelation analysis. A result is extracted which is indicative of a property of the fluid, such as a height of a condensed fluid, a cavitation of the condensed fluid, and a surface perturbation of the condensed fluid.

Similar ultrasonic range measurement techniques are well known in the art, and have been used in wide range of applications, including sonar, robotic ranging, and medical imaging. In principal, a single piezoelectric transducer is used for sending and receiving an ultrasound wave (signal) via piezoelectric effects, and a thickness value of a target bulk (e.g. fluid medium) is obtained by measuring a trip time of the ultrasonic wave multiplied by a corresponding wave velocity in the medium divided by two (taking into account the ultrasonic wave path, back and forth, through the target bulk).

The above measurement methods based on a single transducer generally work when the surface of the fluid is normal, or substantially normal, to the propagating wave front of the ultrasound wave (e.g., steady-state condition), otherwise, as in the case of a fluid under turbulent flow conditions, the ultrasonic wave is refracted or scattered and is not returned for detection at the single (piezoelectric) transducer.

Therefore, there is a need for systems and methods that can provide improved and accurate measurement of fluid contents of piping systems not only under steady-state conditions, but also under turbulent flow conditions.

SUMMARY

According to one embodiment the present disclosure, a system for monitoring fluid level in a pipe under steady-state and turbulent flow conditions is presented, the system comprising: a plurality of multiplexed piezoelectric transducers separated from a fluid by a wall of a pipe, each configured, when activated, to transmit an ultrasound signal through the pipe and receive a corresponding ultrasound signal that is reflected by a surface of the fluid in the pipe that is away from the wall of the pipe, transmission and reception of the ultrasound signal defining a corresponding time-of-flight; a multiplexer unit coupled to the plurality of multiplexed piezoelectric transducers, the multiplexer unit configured to activate and deactivate each of the plurality of said transducers according to an activation sequence; and a signal processor unit coupled to the multiplexer unit, configured to: i) control the activation sequence of the multiplexer unit and receive the ultrasound signal that is reflected by the surface of the fluid, and ii) provide an indication of the fluid level in the pipe based on a time-of-flight associated with a received ultrasound signal that has an energy level greater than a predefined energy level and has a time-of-flight greater than a predefined threshold time.

According to a second embodiment of the present disclosure, a method for monitoring fluid level in a pipe under steady-state and turbulent flow conditions is presented, the method comprising: i) attaching a plurality of multiplexed piezoelectric transducers to a wall of the pipe; ii) activating a transducer of said transducers; iii) based on the activating, transmitting an ultrasound signal through the wall of the pipe; iv) based on the transmitting, receiving a corresponding ultrasound signal that is reflected by a surface of a fluid in the pipe; v) based on the receiving, comparing an energy level of the ultrasound signal to a predefined energy level; vi) based on the comparing, if the energy level is smaller than or equal to the predefined energy level, then deactivate the transducer, activate a next transducer of said transducers, and go to step iii); vii) based on the comparing, if the energy level is greater than the predefined level, then measuring a time-of-flight associated to the transmitting and receiving; and viii) based on the measuring, if the time-of-flight is smaller than or equal to a predefined threshold time, then deactivate the transducer, activate a next transducer of said transducers, and go to step iii); ix) based on the measuring, if the time-of-flight is greater than the predefined threshold time, then using of the time-of-flight as an indication of the fluid level in the pipe.

Further aspects of the disclosure are shown in the specification, drawings and claims of the present application.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

Steam pipes are used in various major metropolitan areas across the world. Health monitoring of these pipes while in operation is critical to public safety. One of the critical requirements of a steam pipe is to monitor the condensed water level through the wall of the pipe. The objective of the system according to the present disclosure is to provide early alert to prevent potential failure of the pipe. The results obtained in both lab and field demonstrate the feasibility and efficiency of system according to the present disclosure. Received signals can be affected by a strong ringing because of reflection from steel pipe interfaces and the local rough outside surface of the pipe, and attenuation causes loss of the reflected amplitude (energy). The amplitude may be significantly affected in service by the dynamic environments that are involved, including vibration of the support structures, ripples of the water surface induced by, for example, fast moving steam, temperature variation, presence of bubbles, potential water hammer effect, etc. The water hammer and other severe water flow conditions may lead to serious consequences including damaged vents, traps, regulators and piping.

Figure 1:
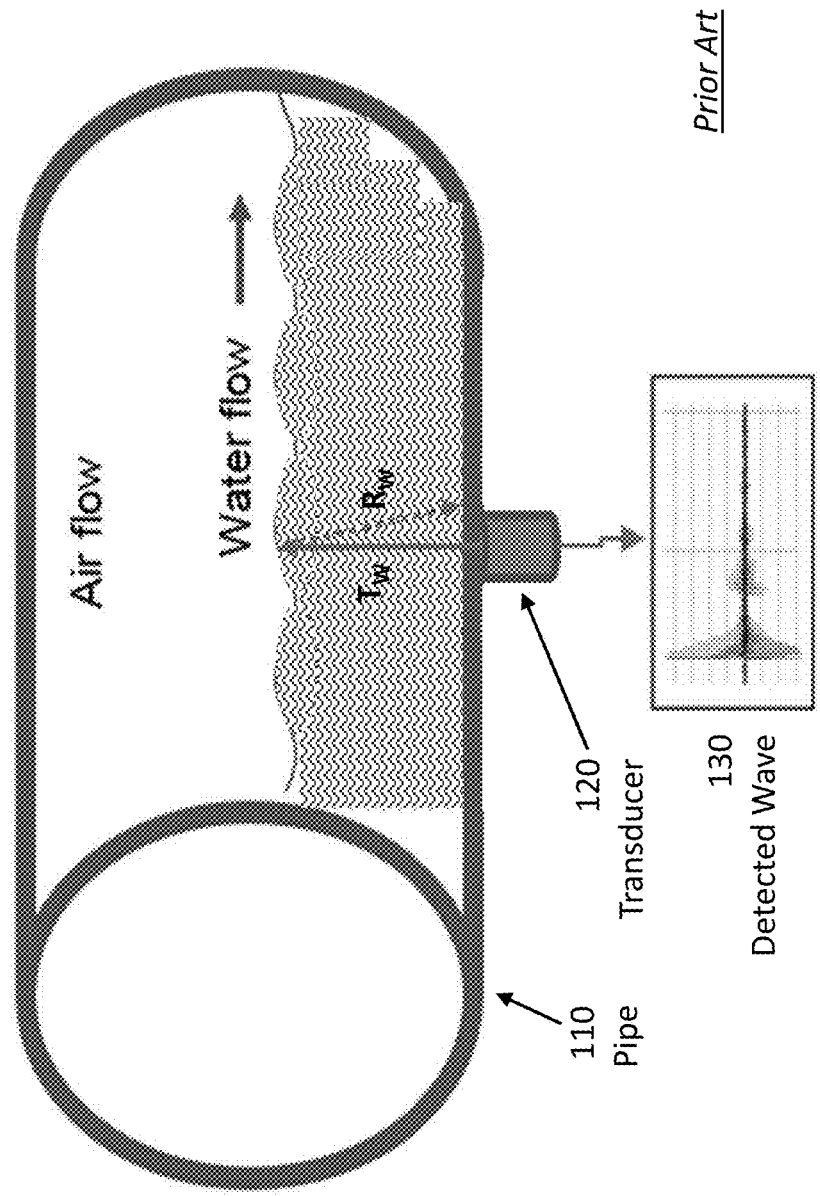
FIG. 1 illustrates a prior art implementation of a single probe system used for measuring a fluid level inside a pipe via a single transducer.

Under turbulent flow conditions, it may be difficult to obtain accurate determination of the fluid (e.g., water) height inside the pipe with a single transducer system, as the fluid surface may have various shapes including wavy, and circumferential around the internal surface of the pipe. FIG. 1 illustrates a prior art implementation (100) of a single probe system used for measuring a fluid level inside a pipe (110) via a single transducer (120), and without penetrating the wall of the pipe (110). More detailed description of such implementation can be found, for example, in the above referenced U.S. Pat. Nos. 8,632,244 B2, 9,404,891 B2, and 9,586,234 B2, the disclosures of which are incorporated herein by reference in their entireties. In particular, such prior system is shown in a case where the fluid inside a pipe (110) is under turbulent flow conditions, in which case a surface of the fluid inside the pipe (110) is not necessarily normal to a propagating wave front of a transmitted ultrasound signal, $T_W$, by the transducer (120). Consequently, the signal, $R_W$, reflected by the surface of the fluid back towards the transducer (120) may be refracted and/or scattered, and as shown in FIG. 1, not returned to the transducer (120), or returned only partially to the transducer (120), so that a detected signal energy at the transducer cannot be representative of a time-of-flight (TOF) measurement used to derive a level (e.g., height) of the fluid inside the pipe (110). This can lead to erroneous real-time measurement of the fluid height inside of the pipe (110), and therefore, rendering such single transducer-based system ineffective for early alert provision.

Figure 2:
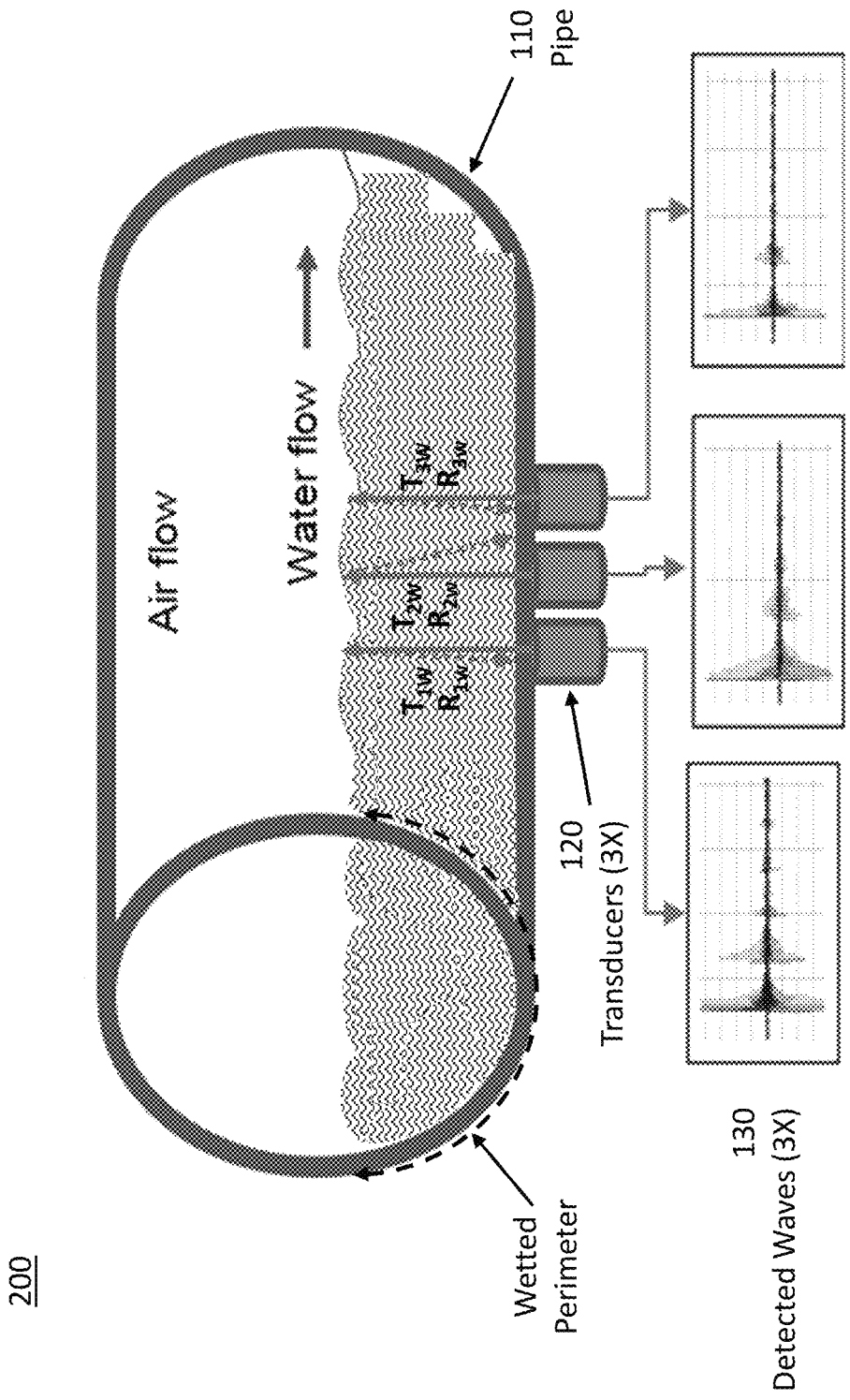
FIG. 2 shows an exemplary embodiment according to the present disclosure of a multi-probe system for measuring a fluid level inside a pipe via a plurality of transducers operable in a multiplexed fashion.

FIG. 2 shows an exemplary embodiment according to the present disclosure of a multi-probe system (200) for measuring a fluid level inside a pipe (110) via a plurality of transducers (120) operable in a multiplexed fashion, wherein the plurality of transducers do not penetrate the wall of the pipe (110). By multiplexing activation of the transducers (120), so to successively and in sequence transmit a signal ($T_{1W}$, $T_{2W}$, $T_{3W}$) and receive a reflected signal ($R_{1W}$, $R_{2W}$, $R_{3W}$), multiple indications of fluid level can concurrently be taken at a location of the pipe, which can therefore allow the multi-probe system (200) to provide real-time non-destructive fluid level (e.g., height) determination under steady-state (static) and turbulent flow (dynamic) conditions. It should be noted that an indication of the fluid level is provided via TOF data of ultrasound signals (e.g., for each pair of ($T_{nW}$, $R_{nW}$), with a sufficiently high energy of detection, that are transmitted and received by each of the transducers (120) when activated. It should also be noted that an overall sweep time in the multiplexing of all the transducers (120) and detecting of associated reflected (ultrasound) signals can be orders of magnitude faster than the travel time of the fluid inside the pipe, and therefore, the detected TOF data can be considered representative of a fluid level at a given time.

With further reference to the multi-probe system (200) of FIG. 2, the detected signals ($R_{1W}$, $R_{2W}$, $R_{3W}$) by the multiple transducers (120) can provide comparable and complementary data to support, verify, and validate the fluid level measurement even under turbulent flow conditions. Any uncertainty in measurement can also be eliminated through crosschecking of the detected signals and elimination of outlier data. Such outlier data may result from such causes as, for example, return signal scattering and/or refraction via fluid surface non-uniformities, and/or degradation of the pipe external surface and/or internal pipe corrosion. Additionally, placing the multiple transducers (120) along the pipe's longitudinal and circumferential directions, as shown in FIGS. 5-8 later described, allows the system (200) according to the present teachings to measure two-dimensional fluid (e.g., water) height profile and, if desired, derive/store corresponding fluid surface patterns for further analysis. According to an embodiment of the present disclosure, such surface patterns can be used for cluster analysis to identify potential disaster flow conditions with incorporated machine learning code.

As noted above, the multi-probe system (200) of FIG. 2 can be used to measure fluid level inside the pipe (110) under steady-state and turbulent flow conditions. According to an exemplary embodiment, the Channel Reynolds number $Re_{Channel}$, well known to a person skilled in the art, can be used in a partially filled pipe (110) to gauge a degree of turbulence according to the following known in the art expression (1):

$$Re_{Channel} = \frac{\rho V R_{hydraulic}}{\mu} \quad (1)$$

where $R_{hydraulic}$ is the hydraulic radius defined by a cross-sectional area of the flow of the fluid inside the pipe divided by a wetted perimeter, V is the flow of the fluid speed, µ is the dynamic viscosity of the fluid, and ρ is the density of the fluid. A person skilled in the art would know that, as shown in FIG. 2, a wetted perimeter is the perimeter of a cross sectional area in the pipe that is "wet" by the fluid. Such wetted perimeter can be calculated given knowledge of a radius of the pipe at the cross sectional area, and a height of the fluid in the pipe at the same area.

As used herein, a steady-state flow condition can be represented by an average Channel Reynolds number that is smaller than $10^4$, calculated as a mean Reynolds number within a testing period. As used herein, the term "steady-state flow" can indicate a condition where the fluid height inside the pipe is relatively steady compared to that of a highly fluctuating height obtained in a turbulent flow condition where the averaging Channel Reynolds can be larger than $10^6$. As used herein, a flow condition represented by an averaging Channel Reynolds number that is between $10^4$ and $10^6$ is defined as a transitional flow condition. A person skilled in the art would appreciate capability of the multi-probe system (200) according to the present teachings to measure, in real-time, fluid level inside the pipe (110) under steady-state, transitional, and turbulent flow conditions.

Figure 3A:
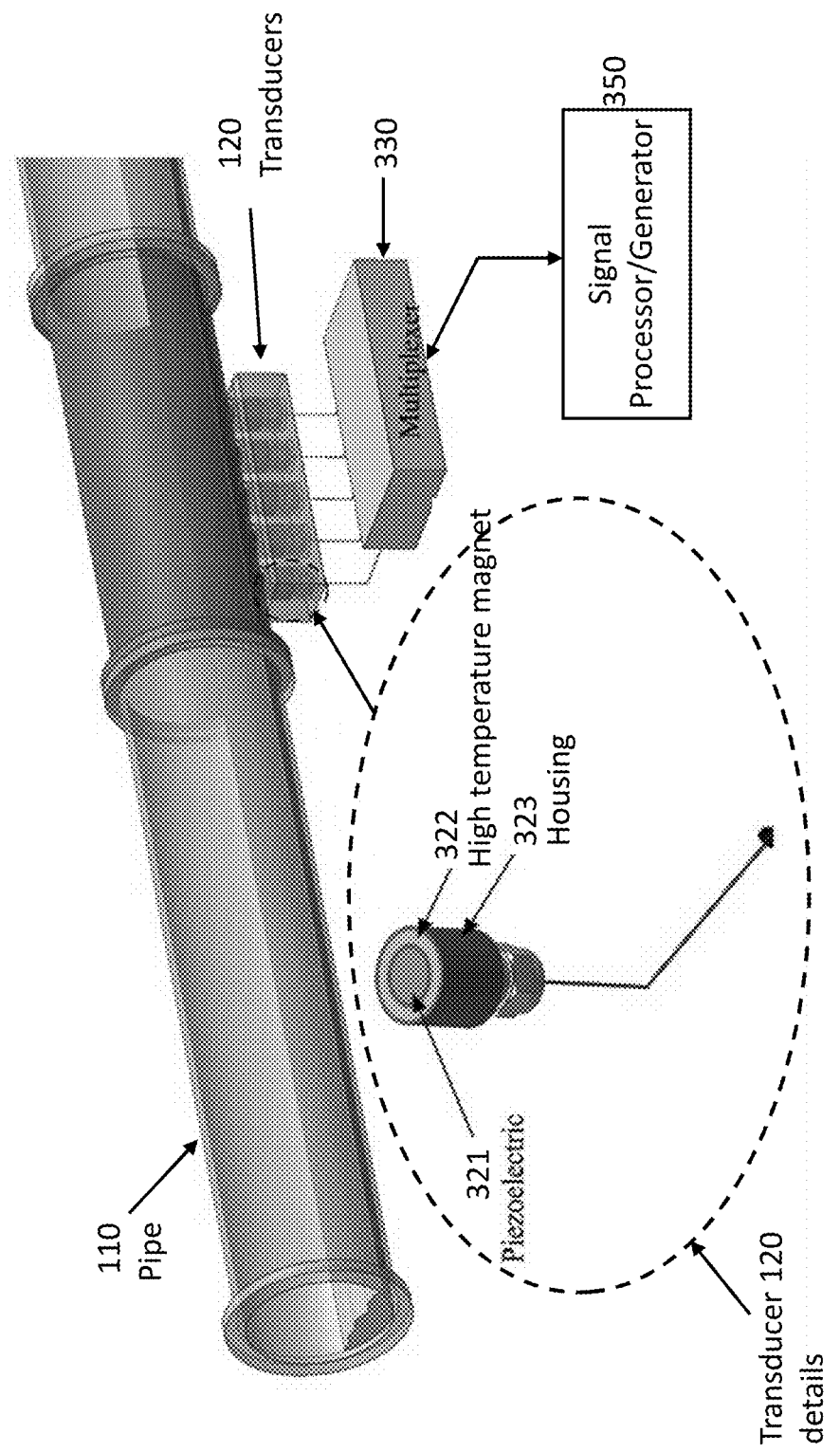
FIG. 3A shows further details of the exemplary embodiment of FIG. 2, inclusive of transducer details, multiplexing details and signal generation and analysis details.

FIG. 3A shows further details of the exemplary multi-probe system of FIG. 2, inclusive of details of a transducer (120) of the plurality of transducers, a multiplexer unit (330) configured to control the multiplexing of the plurality of transducers (120), and a signal processor/generator unit (350) configured to generate signals for transmission by the transducers (120) and process/analyze signals received by the transducers (120). As shown in the details of FIG. 3A, according to an embodiment of the present disclosure, the transducer (120) may comprise a piezoelectric element (321) and a high temperature magnet (322) (e.g., withstands temperatures up to 250° C.) fitted within a housing (323). According to an embodiment of the present disclosure, the high temperature magnet (322) has a high pull force which can advantageously simplify mounting of the transducer (120) to the pipe (110), instead of, for example, of using a strapping mechanism, which although possible, can be less practical in field installations. The piezoelectric element (321) can be a transducer used to launch (transmit) an ultrasonic probe signal into the pipe (110) that is used in pulse-echo manner to measure a corresponding TOF. Reflected (echoed) ultrasonic signals can be captured by the same transducer and a corresponding electrical signal fed to the multiplexer unit (330) for validation and processing by downstream signal processor/generator unit (350). Further information of such method of generating and detecting of the ultrasonic signal by a same transducer can be found, for example, in the above referenced U.S. Pat. Nos. 8,632,244 B2, 9,404,891 B2, and 9,586,234 B2, the disclosures of which are incorporated herein by reference in their entireties.

Figure 3B:
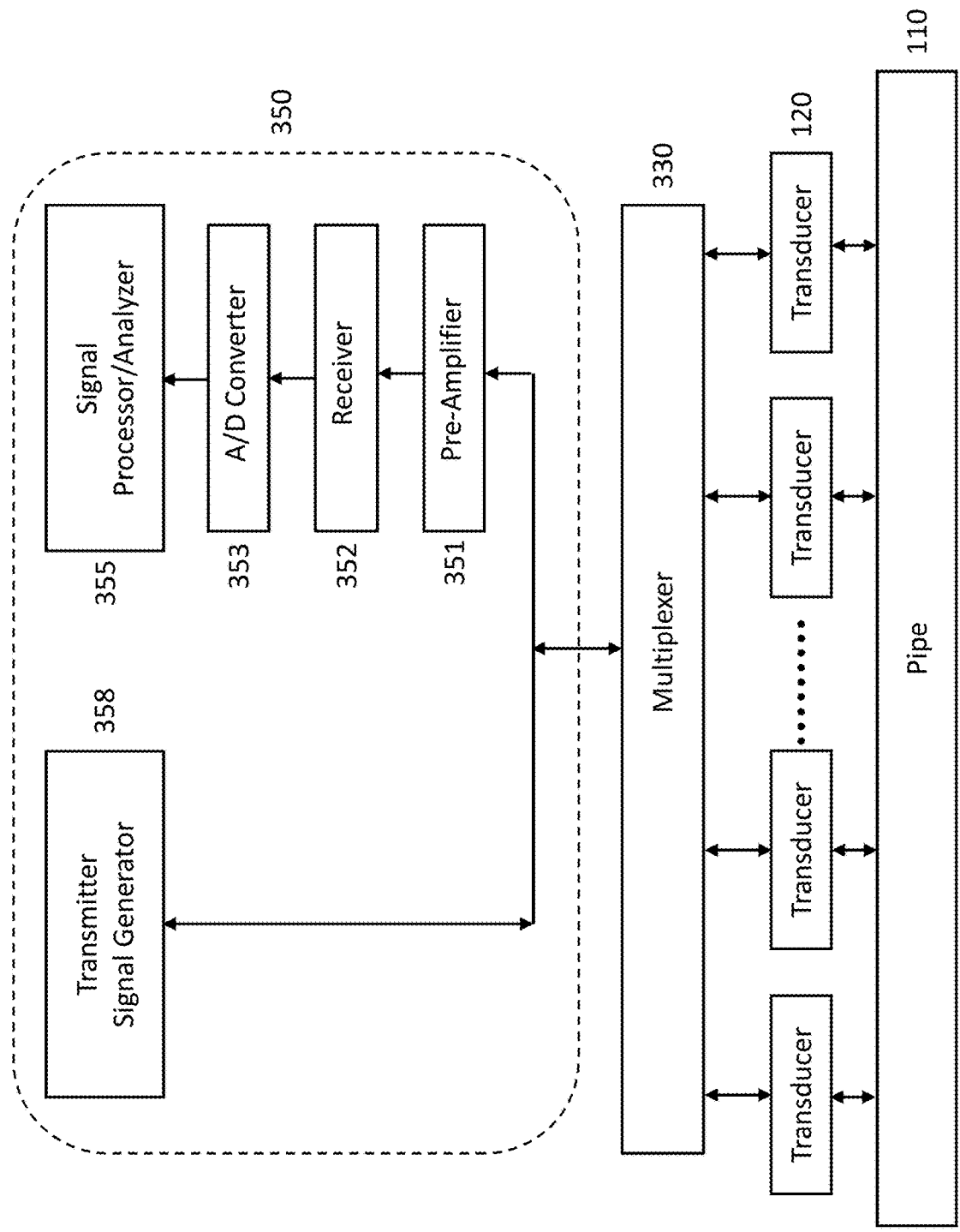
FIG. 3B shows an exemplary signal processing block diagram of the embodiment according to the present disclosure shown in FIG. 3A.

With further reference to FIG. 3A, a multiplexing sequence of the multiplexer unit (330) for activation (and therefore deactivation) of the multiple transducers (120) can be controlled by the signal processor/generator unit (350). As shown in FIG. 3B, the signal processor/generator unit (350) may include a signal processor/analyzer module (355), inclusive of associated hardware, firmware and software, for analyzing the detected signals and determination of measured fluid level with possible links/transmission to monitoring devices/system. Also included in the signal processor/generator unit (350) may be a pre-amplifier (351) to amplify detected signals, a receiver (352) to further condition (e.g., filtering) the detected and amplified signal, an A/D converter (353) to digitize the amplified/conditioned detected signal for further processing by the signal processor/analyzer module (355). Finally, a transmitter/signal generator module (358) may be used in the signal processor/generator unit (350) to generate pulse signals that are provided to the transducers (120) for generation of appropriate ultrasound signals.

With continued reference to FIG. 3A, the multiplexer (330) can be configured to transmit and receive pulse signals to/from any of the transducers (120). In other words, the combination of the multiplexer (330) and the transducers (120) form a multi-channel system where each channel, associated to each transducer (120), can transmit and receive pulse signals independently from the other channels. It should be noted that the transducers (120) may be of a same type and therefore operating at a same pulse frequency and nominal amplitude or may be of different types and therefore operating at different pulse frequencies and nominal amplitudes. The transmitter/signal generator module (358) can generate pulse signals at frequencies and amplitudes according to specific requirements of each of the transducers (120). According to a preferred embodiment of the present disclosure, the transducers (120) operate at frequencies equal to or greater than 2.25 MHz, such as, for example, 2.25 MHz, 5 MHz, 10 MHz, and beyond. A person skilled in the art would understand advantages of using higher frequencies, including provision for an increased detection resolution of the fluid level in the pipe.

Figure 3C:
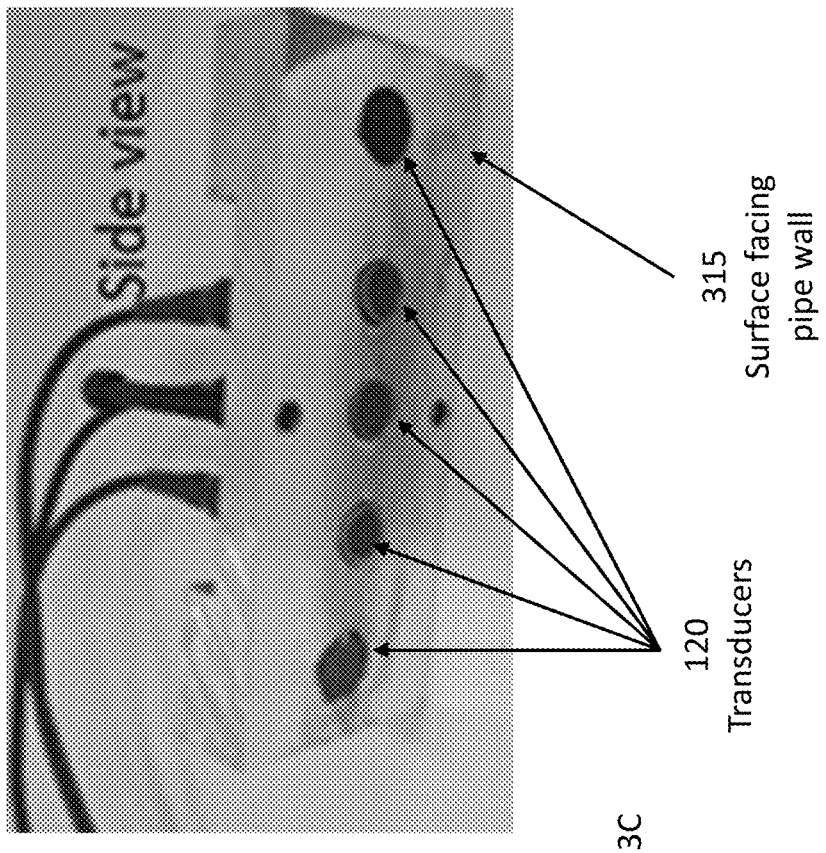
FIG. 3C shows bottom and side views of a mounting fixture according to an embodiment of the present disclosure that is adapted for attaching a plurality of transducers to a surface of a pipe and independently aligning each of said transducers.
Figure 3C:
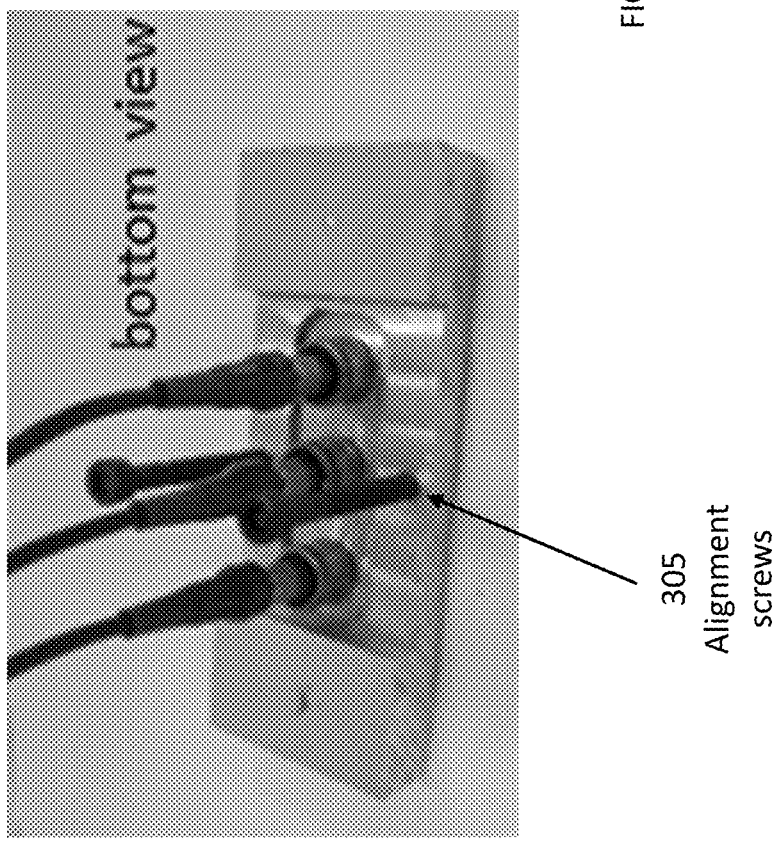

FIG. 3C shows bottom and side views of a mounting fixture according to an embodiment of the present disclosure that is adapted for attaching the transducers (120) to a surface of the pipe (110), such as, for example, a surface of an outer wall of the pipe, and aligning of said transducers independently of a local shape of said surface. In the mounting fixture shown in FIG. 3C, spacing is provided between the transducers. In addition, such fixture can include two (or more) screws (e.g., socket head screws) to adjust an angle of the surface (315) of the fixture relative to a wall of the pipe where the fixture is attached. The screws allow for stabilization of the fixture against a curved surface of the pipe and alignment of the transducers (12) according to a position that provides strongest received signal reflections.

Figure 4:
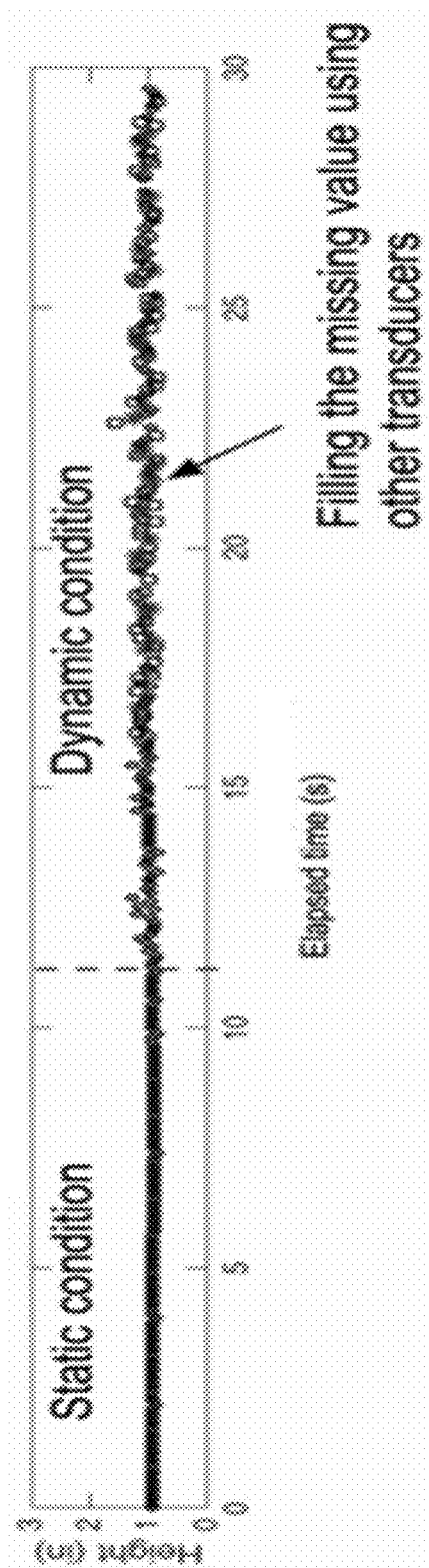
FIG. 4 shows exemplary real-time fluid level data detected via the multi-probe system of FIG. 2 for both cases of steady-state (static) and turbulent flow (dynamic) conditions of the fluid.

FIG. 4 shows exemplary real-time fluid level (e.g., height) data detected via the multi-probe system (200) of FIG. 2 for both cases of steady-state (static) and turbulent flow (dynamic) conditions of the fluid inside the pipe (110). Such experimental data show that using multiple transducers (120) according to the present teachings allows for effective real-time measurements during static and high dynamic water surface conditions. Applicant of the present disclosure consistently obtained accurate results during multiple tests conducted under various dynamic conditions, including steady-state, transitional, and turbulent flow, as well as under various pipe inclinations (e.g., angle of a longitudinal direction of the pipe with respect to a horizontal plane). Such tests have been done in a testbed, where airflow within a pump pushing a fluid through a pipe and on/off duty cycle of the pump were controlled to create desired and observable (e.g., through camera, eye) fluid flow conditions inside the pipe.

For example, turbulent flow condition is generated in the testbed by controlling, for example via a fan, the airflow inside the pump so to generate, and observe, various levels of turbulent fluctuation of the fluid inside the pipe. Under such controlled dynamic conditions, one or more of the plurality of transducers can accurately capture real-time fluid level data, which data can be used to fill (e.g., via interpolation/prediction algorithms) any missing data so to provide an increased resolution of the fluid level profile during a duration of the data capture. Applicant of the present disclosure compared the measured fluid levels derived from the captured data and compared with those observed from synchronized video snap shots of the fluid profile in the pipe. Results have shown an average error between the measured fluid level and the observed fluid level of less than 5%.

Figure 5:
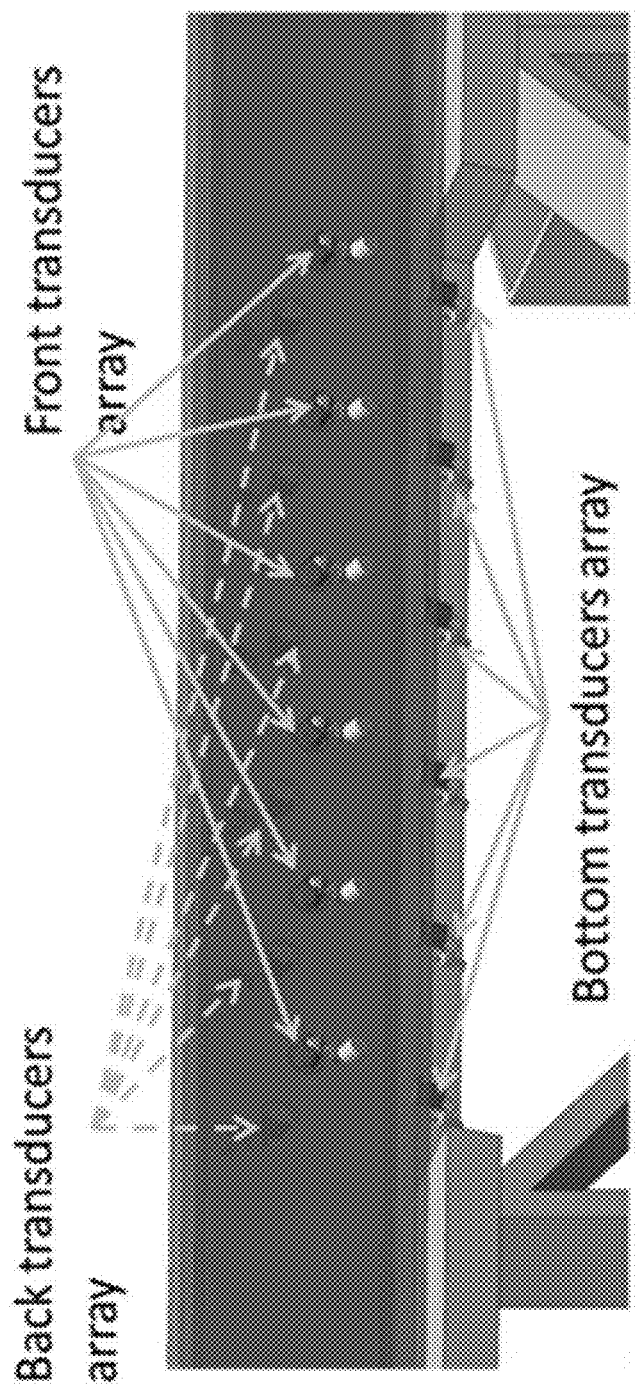
FIG. 5 shows an exemplary embodiment according to the present disclosure of an arrangement of the plurality of transducers of the multi-probe system of FIG. 2, wherein the plurality of transducers are arranged according to longitudinal arrays of transducers placed at different circumferential positions relative to the pipe.
Figure 6:
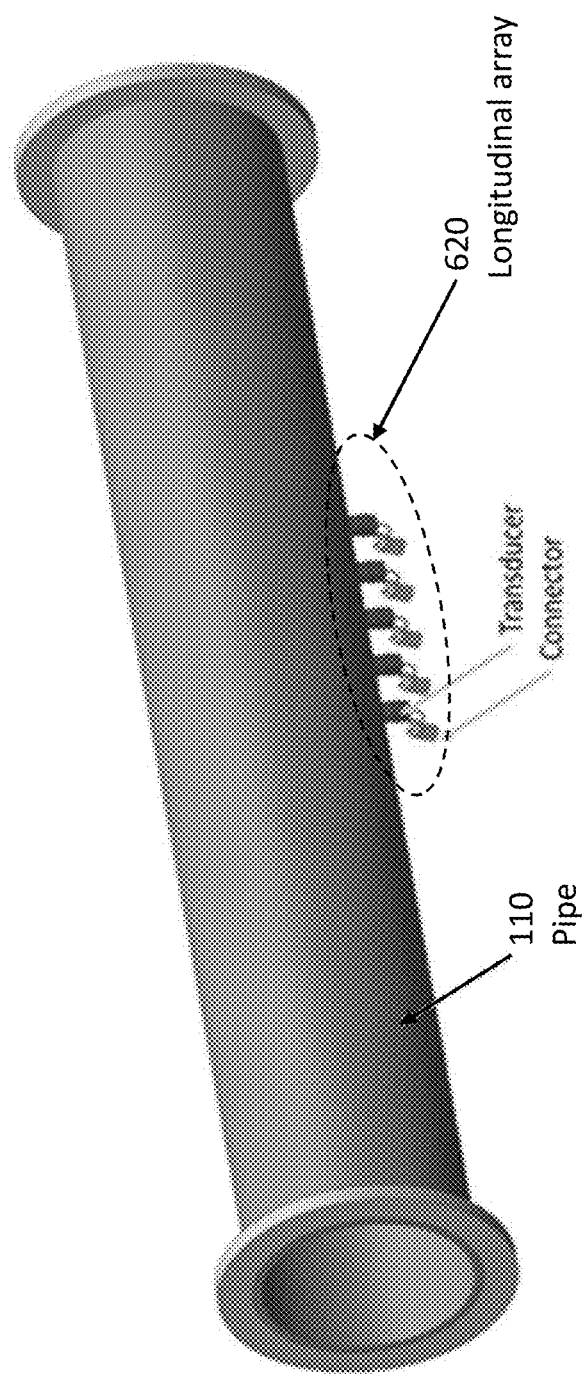
FIG. 6 shows an exemplary embodiment according to the present disclosure of an arrangement of the plurality of transducers of the multi-probe system of FIG. 2, wherein the plurality of transducers are arranged according to a single longitudinal array of transducers placed at a fixed circumferential position relative to the pipe.
Figure 7:
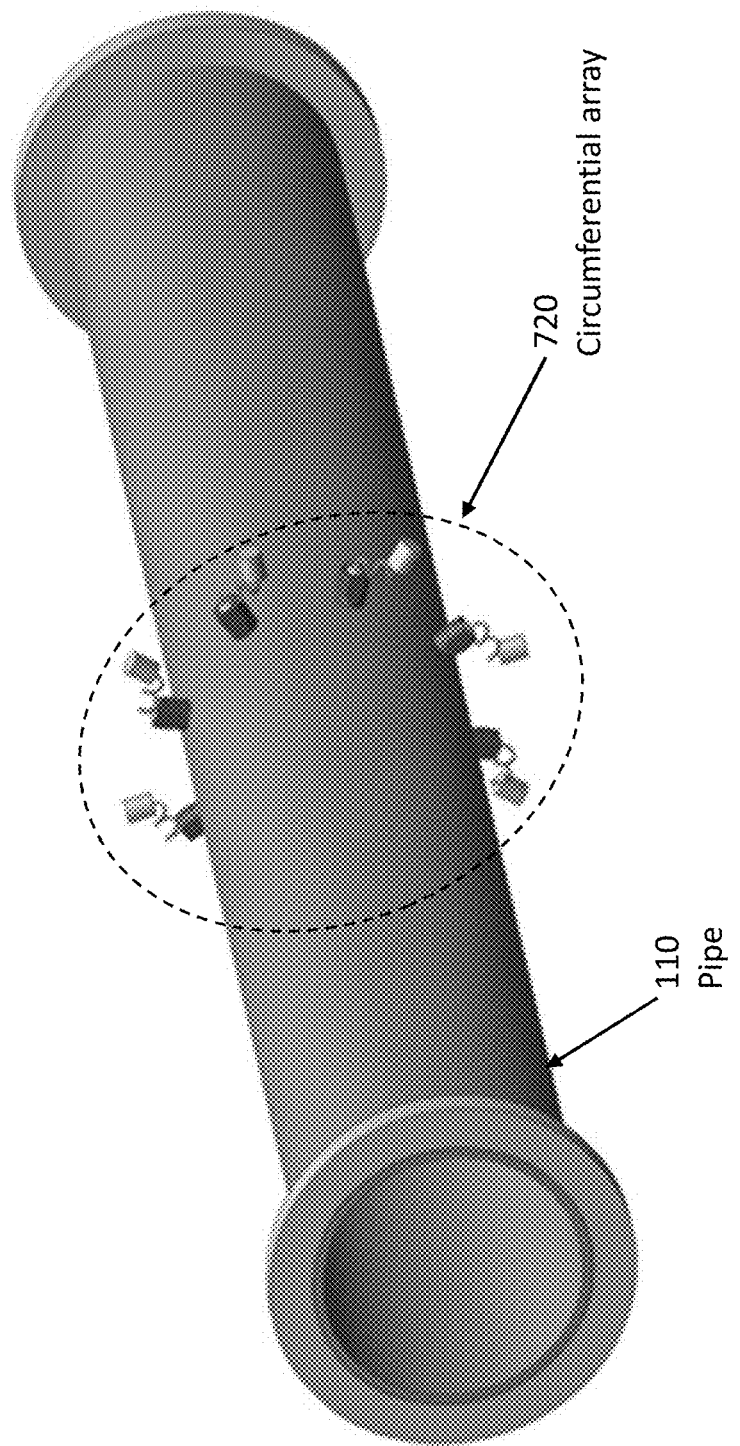
FIG. 7 shows an exemplary embodiment according to the present disclosure of an arrangement of the plurality of transducers of the multi-probe system of FIG. 2, wherein the plurality of transducers are arranged according to a single circumferential array of transducers placed at a fixed longitudinal position of the pipe.
Figure 8:
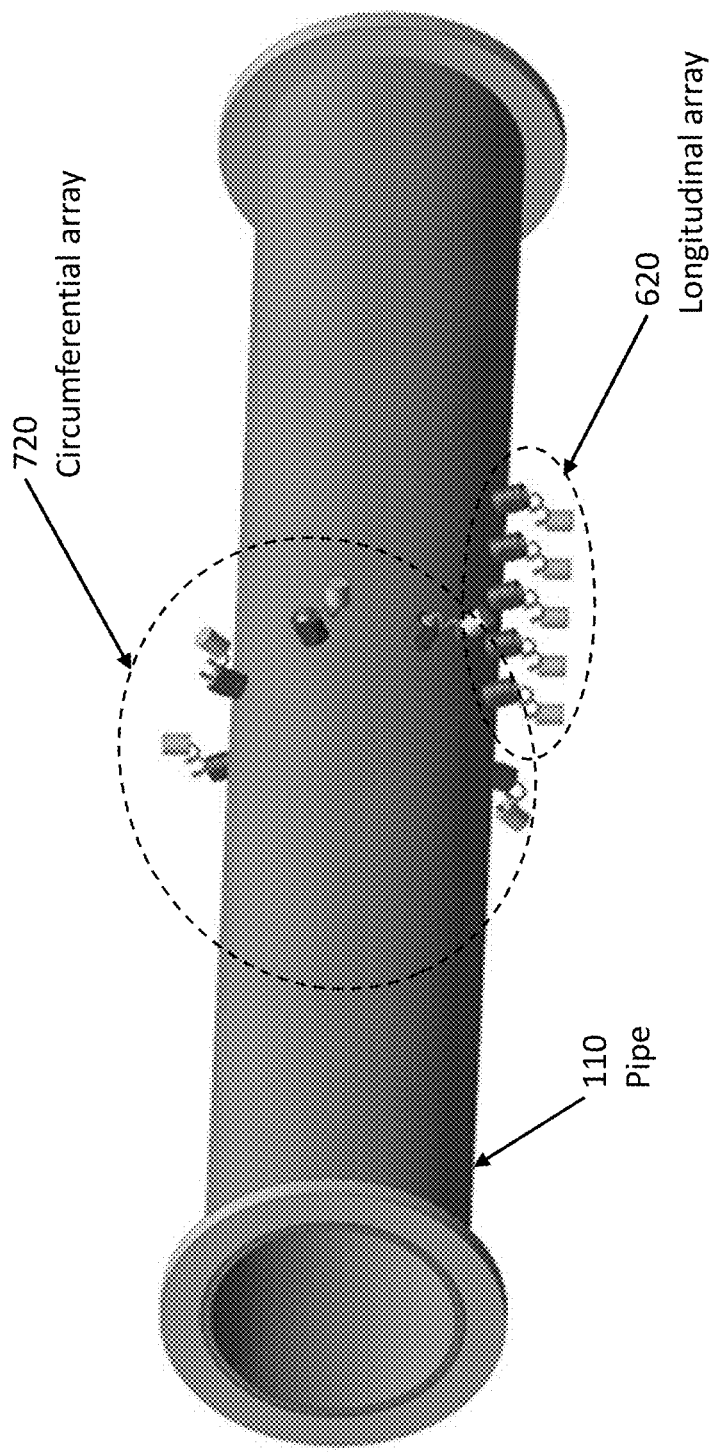
FIG. 8 shows an exemplary embodiment according to the present disclosure of an arrangement of the plurality of transducers of the multi-probe system of FIG. 2, wherein the plurality of transducers are arranged according to a combination of longitudinal arrays per FIG. 6, and circumferential arrays per FIG. 7.

As described above, the transducers (120) of the multi-probe system (200) according to the present teachings can be arranged around walls of the pipe (110) according to various configurations. Some exemplary configurations are shown in FIGS. 5, 6, 7 and 8. As shown in FIG. 5, according to an exemplary embodiment of the present disclosure, the plurality of transducers (120) may be arranged according to one or more longitudinal arrays of transducers placed at different circumferential positions relative to the pipe. For example, there can be a set of longitudinal arrays placed on a bottom region of the pipe (110), a set of longitudinal arrays placed on a front region of the pipe (110), and a set of longitudinal arrays placed on a back region of the pipe (110), where the bottom, front and back regions are referenced to a side view of the pipe (110) that reveal the front region, as shown in FIG. 5. In other words, each of the sets of longitudinal arrays is positioned at a substantially fixed circumferential (e.g., angular) position of the pipe (110). As shown in FIGS. 6, 7 and 8, according to a further exemplary embodiments of the present disclosure, there can be, respectively, a single longitudinal array of transducers placed at a fixed circumferential position of the pipe (e.g., bottom region), a single circumferential array of transducers arranged circumferentially around the wall of the pipe (110) at a substantially fixed longitudinal position of the pipe, and a combination of a longitudinal array and a circumferential array that share a longitudinal and a circumferential position of the pipe (110).

With further reference to the exemplary arrays of transducers shown in FIGS. 5, 6, 7 and 8, a choice of arrangement of such arrays may be based on expected/possible fluid surface profiles in the pipe, including, for example, a longitudinal wave with respect to a flow of the fluid inside of the pipe, a traverse wave with respect to the flow of the fluid inside of the pipe, and a circumferential profile around the internal surface of the pipe.

According to a further embodiment of the present disclosure, the multi-probe system according to the present disclosure comprises a multiplexing sequence of the plurality of transducers (120) coupled with an adaptive envelope extraction signal processing algorithm that in combination, allow a robust fluid level detection in all flow conditions. Such algorithm essentially controls a sequence of transmitting pulses, from the multiplexer (330 of FIG. 3) to the transducers (120) and applies an appropriate time delay to establish valid measurement data (e.g., TOF). The A/D converter (353 of FIG. 3) converts received analog signals from the receiver (352 of FIG. 3) into digital signals, and the signal processor/analyzer module (355 of FIG. 3) compares the energy level (e.g., amplitude) of each of the received signals with a predefined energy level (e.g., E* of FIG. 9). Responsive to a pulse signal transmitted via a first transducer (120) of the plurality of transducers, an energy level of a corresponding received signal (i.e., echo) is measured and compared to the predefined energy level. If the measured energy level is equal to or lower than the predefined energy level, such received signal is disqualified as a measurement data point and a second transducer (120) of the plurality of transducers is selected/activated to transmit a pulse signal whose echo is subsequently subjected to same comparison. Such sequence of activating, transmitting, receiving, comparing, disqualifying and deactivating, continues until the reflected echo exceeds the predefined energy level and corresponding received signal is qualified as a measurement data point with a given timestamp. After such sequence, a similar next sequence can be started for a new measurement data point with a different timestamp. Further details of such algorithm are shown in the flowchart of FIG. 9.

Figure 9:
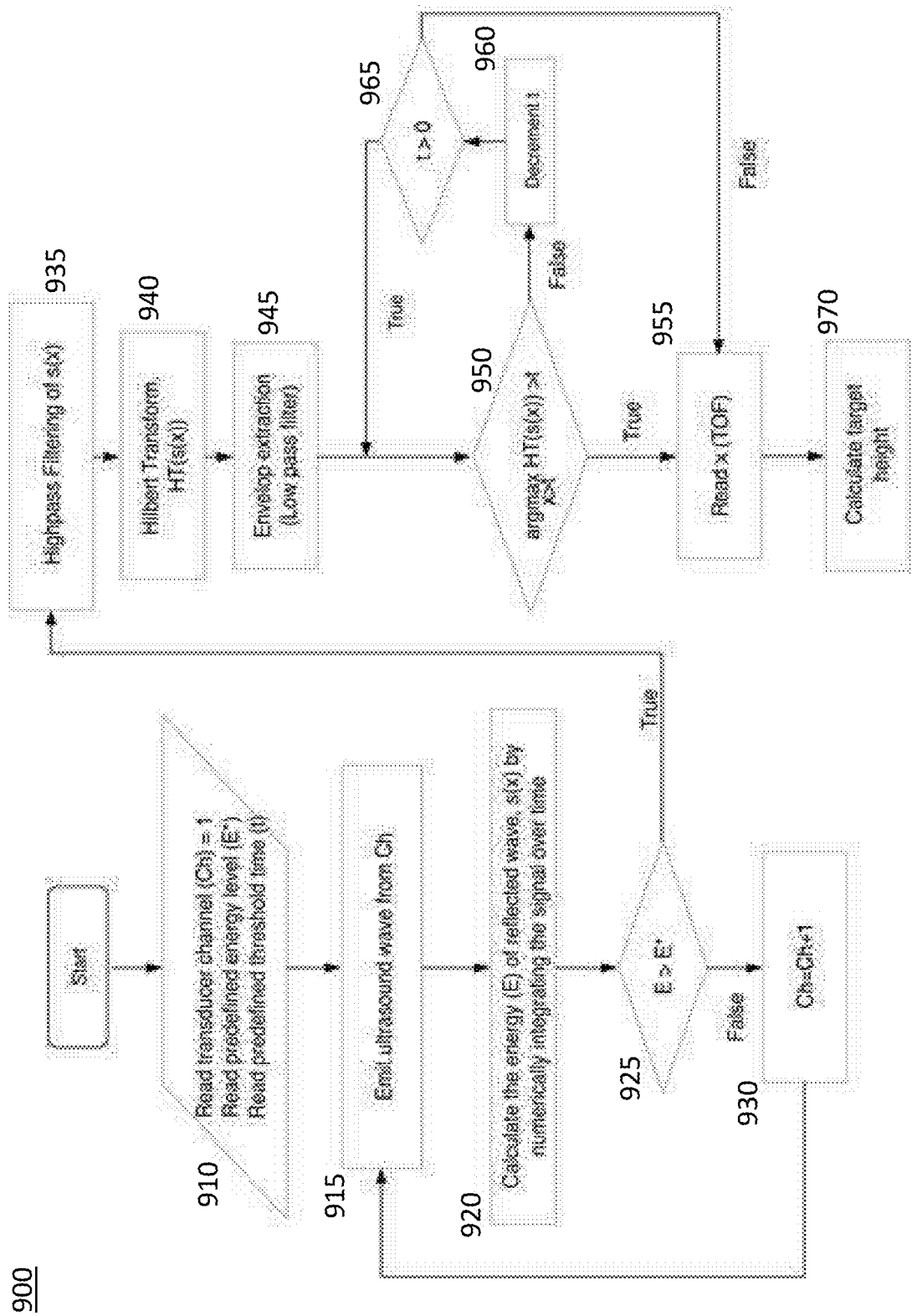
FIG. 9 shows an exemplary flowchart for measuring the fluid level inside a pipe via multiplexing of the plurality of transducers of the multi-probe system of FIG. 2.

FIG. 9 shows process steps of an exemplary flowchart (900) for measuring the fluid level inside a pipe (110) via multiplexing of the plurality of transducers (120) of the multi-probe system (200) of FIG. 2. According to an embodiment of the present disclosure, the predefined energy level E* is chosen to be a minimum energy level that corresponds to the energy for a case where there is no fluid inside the pipe. According to an embodiment of the present disclosure, the minimum energy is determined by integrating the received signal over a time window T that extends from a predefined threshold time, t, to an end of acquired time. The predefined threshold time, t, can be considered as the time of detection of a minimum amplitude (energy) of a first reflection (which is received from the pipe). Below the predefined threshold time, reflections from the pipe cannot be distinguished from the reflections from the water top surface due to overlapping of corresponding signals. Accordingly, an energy level that is higher than the minimum energy level includes reflections from the surface of the fluid which can therefore be used for TOF determination. Furthermore, the "end of acquired time" is a parameter (in the time domain) that depends on a size of the pipe and is chosen to be well above an expected TOF and below a travel time of the ultrasound signal from bottom to top of the pipe (e.g., assuming pipe is filled with fluid from bottom to top). For example, in a case of a 6" (approximately 0.1524 m) pipe filled with water, the end of acquired time can be chosen to be below t=2*0.1524 m/(1540 m/s)=~200 microseconds, where 1540 is the speed of sound in water.

In steps (915, 920, 925, 930), when the energy E of a received (e.g., detected, echoed) signal responsive to a transmitted signal from an activated transducer (i.e., step 915, channel Ch) is equal to or below the predefined energy E* (step 925), the algorithm considers that there is no reflected signal from the target (e.g., fluid+pipe wall), and a different channel is activated (step 930, Ch=Ch+1), emitting and receiving the ultrasound wave signal. Once a received signal (e.g., echo) has a relatively high signal strength (i.e., step 925, E>E*), an adaptive envelope extraction signal processing algorithm (i.e., steps 940, 945) that combines with high pass filtering (i.e., step 935) and autocorrelation (i.e., steps 950, 955, 960, 965) is applied on the received (echoed) signal to determine the time-of-flight (TOF) data that is indicative of the fluid level inside the pipe (110).

With further reference to the flowchart of FIG. 9, According to an embodiment of the present disclosure, high pass filtering (steps 935) and autocorrelation (steps 950, 955, 960, 965) of the received signal advantageously allow accurate determination of the TOF (time-of-flight) measurement in spite of presence, in the received signal, of low frequency noise and reflections from the pipe that can distort the received signal. According to an exemplary embodiment of the present disclosure, a ten-order Butterworth-type high-pass filter with a cutoff frequency near a resonant frequency of the ultrasonic transducer (120) can be used in step (935). Such filter can allow filtering out of the low frequency noise, inclusive of ambient noise and other low frequency interferences.

With continued reference to the flowchart (900) of FIG. 9, according to an exemplary embodiment of the present disclosure, the envelop extraction step (945), can comprise applying of a low pass filter on the signal generated during the prior Hilbert transformation step (940), so to eliminate high frequency reflection signals that may be generated by the Hilbert transformation due to the presence of the pipe wall. Such reflection signals can generate many local peaks and valleys that can effectively provide a ringing effect to a detected envelope signal, thus making a determination of the fluid level difficult. By low pass filtering the signal, such ringing effect can be filtered out and therefore an accurate measurement of the fluid level be obtained. Since the ringing of signal envelope is caused by the reflections within the pipe wall, a reflection frequency $f_{ref}=1/T_{ref}$ is used for the cut-off frequency in the low pass filter used in the step (945), where the reflection period $T_{ref}$ of a reflected signal can be obtained from a round trip time of the ultrasonic wave propagating between an outer pipe wall (e.g., an outer wall surface of the pipe) in contact with the transducer and an inner pipe wall (e.g., an inner wall surface of the pipe) in contact with the fluid.

Steps (950, 955, 960, 965) of the flowchart (900) of FIG. 9 determine a TOF measurement value from the extracted Hilbert envelop provided in step (945). This is done by finding, via steps (950, 955, 960), a local maximum time (x) of a second signal group and a predetermined threshold time (t) of the first echo from the pipe wall. As shown in steps (950, 955, 960), the local maximum time x can be found by searching for a time that is above the threshold time t. Once the local maximum time x is found, then it is considered to be the TOF measurement (step 965), from which a corresponding fluid level can be generated (step 970). A person skilled in the art would appreciate that steps 950-965 allow distinguishing a reflected signal from the fluid surface from a reflected signal from the pipe walls, and therefore allow for an accurate measurement of the TOF.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A system for monitoring fluid level in a pipe under steady-state and turbulent flow conditions, the system comprising:
a plurality of multiplexed piezoelectric transducers separated from a fluid by a wall of a pipe, each configured, when activated, to transmit an ultrasound signal through the pipe and receive a corresponding ultrasound signal that is reflected by a surface of the fluid in the pipe that is away from the wall of the pipe, transmission and reception of the ultrasound signal defining a corresponding time-of-flight;
a multiplexer unit coupled to the plurality of multiplexed piezoelectric transducers, the multiplexer unit configured to activate and deactivate each of the plurality of said transducers according to an activation sequence; and
a signal processor unit coupled to the multiplexer unit, configured to:
i) control the activation sequence of the multiplexer unit and receive the ultrasound signal that is reflected by the surface of the fluid, and
ii) provide an indication of the fluid level in the pipe based on a time-of-flight associated with a received ultrasound signal that has an energy level greater than a predefined energy level and has a time-of-flight greater than a predefined threshold time.

2. The system according to claim 1, wherein the signal processor unit controls the activation sequence by deactivating an activated transducer of the plurality of multiplexed piezoelectric transducers and activating a deactivated transducer of the plurality of multiplexed piezoelectric transducers when:
the energy level of the received ultrasound signal associated to the activated transducer is smaller than or equal to the predefined energy level, or
the time-of-flight associated to the received ultrasound signal is smaller than or equal to the predefined threshold time.

3. The system according to claim 1, wherein the predefined energy level is based on an integration of a received signal over a time window that starts from the predefined threshold time and extends up to an end of acquisition time for a case where there is no fluid in the pipe.

4. The system according to claim 1, wherein the ultrasound signal has a frequency in a range of 2.25 MHz and above.

5. The system according to claim 1, wherein the plurality of multiplexed piezoelectric transducers are attached to an exterior wall of the pipe by way of magnets having high pull force and capable of withstanding a temperature of up to 250° C.

6. The system according to claim 1, further comprising a mounting fixture, wherein:
the plurality of multiplexed piezoelectric transducers are attached to the mounting fixture, and
the mounting fixture is adjustably attached to a surface of an exterior wall of the pipe.

7. The system according to claim 1, wherein:
the plurality of multiplexed piezoelectric transducers are arranged on an exterior wall of the pipe according to one or more longitudinal array of transducers, and
the signal processor unit is configured to provide a two-dimensional surface profile of the fluid in the pipe based on the time-of-flight associated to transducers of the one or more longitudinal arrays of transducers.

8. The system according to claim 1, wherein:
the plurality of multiplexed piezoelectric transducers are arranged on an exterior wall of the pipe according to one or more circumferential arrays of transducers, and
the signal processor unit is configured to provide a circumferential surface profile of the fluid in the pipe based on the time-of-flight associated to transducers of the one or more circumferential arrays of transducers.

9. The system according to claim 1, wherein:
the plurality of multiplexed piezoelectric transducers are arranged on an exterior wall of the pipe according to a combination of one or more longitudinal and circumferential arrays of transducers, and
the signal processor unit is configured to provide a two-dimensional circumferential surface profile of the fluid in the pipe based on the time-of-flight associated to transducers of the one or more longitudinal and circumferential arrays of transducers.

10. The system according to claim 1, wherein averaging channel Reynolds number associated to the turbulent flow condition is larger than $10^6$.

11. The system according to claim 1, wherein the signal processor unit comprises:
a pre-amplifier configured to amplify the ultrasound signal that is reflected by the surface of the fluid; and
an A/D converter that is configured to digitize a signal amplified by the pre-amplifier.

12. The system according to claim 11, wherein the signal processor unit performs over data digitized by the A/D converter, in sequence:
i) high pass filtering,
ii) Hilbert transformation, and
iii) envelop signal extraction, including low pass filtering.

13. The system according to claim 12, wherein:
the low pass filtering is configured to eliminate ringing effects in the envelop signal caused by reflections in walls of the pipe, and
a cut-off frequency, $f_{ref}$, associated to the low pass filtering is equal to $1/T_{ref}$, where Tref is a reflection period of a reflected signal obtained from a round trip time of an ultrasonic signal propagating between the walls of the pipe.

14. The system according to claim 12, wherein the high pass filtering is provided via a ten-order Butterworth-type filter with a cut-off frequency near a resonant frequency of the plurality of multiplexed piezoelectric transducers.

15. A method of using of the system according to claim 1 for monitoring water in a steam pipe, comprising: attaching the plurality of multiplexed piezoelectric transducers to an external surface of the steam pipe.

16. A method for monitoring fluid level in a pipe under steady-state and turbulent flow conditions, the method comprising:
i) attaching a plurality of multiplexed piezoelectric transducers to a wall of the pipe;
ii) activating a transducer of said transducers;
iii) based on the activating, transmitting an ultrasound signal through the wall of the pipe;

iv) based on the transmitting, receiving a corresponding ultrasound signal that is reflected by a surface of a fluid in the pipe;
v) based on the receiving, comparing an energy level of the ultrasound signal to a predefined energy level;
vi) based on the comparing, if the energy level is smaller than or equal to the predefined energy level, then deactivate the transducer, activate a next transducer of said transducers, and go to step iii);
vii) based on the comparing, if the energy level is greater than the predefined level, then measuring a time-of-flight associated to the transmitting and receiving; and
viii) based on the measuring, if the time-of-flight is smaller than or equal to a predefined threshold time, then deactivate the transducer, activate a next transducer of said transducers, and go to step iii);
ix) based on the measuring, if the time-of-flight is greater than the predefined threshold time, then using of the time-of-flight as an indication of the fluid level in the pipe.

* * * * *